(12) United States Patent
Asai et al.

(10) Patent No.: US 10,433,713 B2
(45) Date of Patent: Oct. 8, 2019

(54) ANTI-LEAK VALVE UNIT FOR OVERTUBE

(71) Applicant: SUMITOMO BAKELITE CO., LTD., Tokyo (JP)

(72) Inventors: Hideaki Asai, Tokyo (JP); Shinetsu Harata, Akita (JP); Yoshiki Toyota, Akita (JP)

(73) Assignee: SUMITOMO BAKELITE CO., LTD., Tokyo (JP)

( * ) Notice: Subject to any disclaimer, the term of this patent is extended or adjusted under 35 U.S.C. 154(b) by 0 days.

(21) Appl. No.: 15/490,602

(22) Filed: Apr. 18, 2017

(65) Prior Publication Data

US 2017/0215708 A1    Aug. 3, 2017

Related U.S. Application Data

(63) Continuation of application No. 12/919,138, filed as application No. PCT/JP2009/001258 on Mar. 23, 2009, now abandoned.

(30) Foreign Application Priority Data

Mar. 24, 2008    (JP) .................................. 2008-075345

(51) Int. Cl.
*A61B 1/00*    (2006.01)
*A61B 1/015*    (2006.01)
*A61B 17/34*    (2006.01)

(52) U.S. Cl.
CPC ...... *A61B 1/00137* (2013.01); *A61B 1/00112* (2013.01); *A61B 1/00128* (2013.01); *A61B 1/00135* (2013.01); *A61B 1/00154* (2013.01); *A61B 1/015* (2013.01); *A61B 17/3423* (2013.01); *A61B 1/0014* (2013.01)

(58) Field of Classification Search
CPC ... A61B 1/00137; A61B 1/0014; A61B 1/018; A61B 1/00112; A61B 1/00119; A61B 17/3423; A61M 39/06
See application file for complete search history.

(56) References Cited

U.S. PATENT DOCUMENTS 6,117,068 A * 9/2000 Gourley ............... A61D 19/027
                                                           600/125
2002/0010425 A1 * 1/2002 Guo ...................... A61M 39/06
                                                           604/167.04

FOREIGN PATENT DOCUMENTS

CN    1907513 A  *  2/2007    ......... A61B 17/3421
EP    0 746 348 A1    12/1996
EP    0 784 961 A1    7/1997
(Continued)

*Primary Examiner* — Aaron B Fairchild
(74) *Attorney, Agent, or Firm* — Oblon, McClelland, Maier & Neustadt, L.L.P.

(57) ABSTRACT

An anti-leak valve unit is removably attached to a base end portion of an overtube through which an endoscope is removably insertable. The anti-leak valve unit includes a frame portion attachable to the overtube, a fitting device on the frame portion that is removably engageable with the base end portion, and a valve element provided inside the frame portion. The frame portion and the fitting device can be embodied as first through third interconnected covers and first and second members attached to the first cover at edges thereof. The valve element can be embodied as a flexible member with an annular endoscope insertion port in a flexible elastic portion thereof.

20 Claims, 9 Drawing Sheets

(56) References Cited

FOREIGN PATENT DOCUMENTS

EP           0 994 740 A1    4/2000
JP         2006262968 A  * 10/2006

* cited by examiner

ANTI-LEAK VALVE UNIT FOR OVERTUBE

TECHNICAL FIELD

The present invention relates to an anti-leak valve unit for overtube.

BACKGROUND ART

The overtube is employed for safely and smoothly inserting and removing an endoscope into and from a body cavity (for example, refer to a patent document 1). Normally, an anti-leak valve is attached to a base end portion of the overtube, in order to prevent leakage of air supplied into the body cavity.

Generally, the anti-leak valve used with the overtube is made of a rubber or silicone rubber that can follow up the movement of the endoscope, and fixed to a portion of the overtube or to a grip (for example, refer to a patent document 2).

In the event of executing Endoscopic Mucosal Resection (EMR) which is an operation of endoscopically resecting a mucous membrane of esophagus, stomach, or colon, conventionally a snare is employed for dividing the diseased tissue in the case where the diseased part is large, and since the diseased tissue that has been resected is relatively small, the structure and shape of the endoscope insertion port of the conventional anti-leak valve allows taking out the diseased tissue without damage.

Recently, Endoscopic Submucosal Dissection (ESD), which is an operation of endoscopically dissecting a submucosa of esophagus, stomach, or colon, has rapidly come to be widely adopted. The ESD is generally executed with the endoscope inserted through the inner cavity of the overtube inserted into the body cavity. Then a high-frequency treatment device is made to stick out from the distal end through the forceps channel of the endoscope, and manipulated while moving the endoscope back and forth, up and down, or rotationally with respect to the overtube. Accordingly, a gap is prone to be formed between the valve element of the anti-leak valve attached to the base end portion of the overtube and a proximal end portion of the endoscope. The formation of the gap between the valve element of the anti-leak valve and the endoscope incurs the problem that the air supplied into the body cavity leaks through the gap and the body cavity is thereby deflated, which degrades the visual field of the endoscope. Also, in the case where the air supply to the part to be treated is insufficient, the part cannot be sufficiently inflated, which may make it difficult for the operator to execute the procedure.

Further, in the case of ESD the diseased part is often collectively resected, and hence the diseased part to be extracted is generally larger than in the case of EMR. However, since the endoscope insertion port of the anti-leak valve is relatively small, the extraction of the diseased part with the anti-leak valve attached to the overtube is technically difficult, especially in the case of ESD. More particularly, because of the presence of the anti-leak valve attached to the base end portion of the overtube, the diseased tissue is damaged when the endoscope passes through the anti-leak valve, or the extraction of the entirety of the diseased tissue is disabled.

[Patent document 1] JP-A No. 2005-046273
[Patent document 2] JP-U No. 3129543

DISCLOSURE OF THE INVENTION

The present invention provides an anti-leak valve unit that allows easily extracting a resected diseased tissue from a body cavity in an endoscopic resection such as EMR and ESD, and that prevents leakage of air supplied into the body cavity, despite moving the endoscope in any direction with respect to the overtube.

According to the present invention, there is provided an anti-leak valve unit for overtube, to be removably attached to abase end portion of an overtube to be inserted into a body cavity, the overtube including an inner cavity through which an endoscope can be removably inserted, comprising:

a frame portion to be attached to an outer circumferential surface of the base end portion of the overtube;

a fitting device provided on the frame portion so as to be removably engaged with the outer circumferential surface of the base end portion; and a valve element provided inside the frame portion;

wherein the valve element includes:

an annular endoscope insertion port located at a generally central portion of the valve element so as to be circumferentially fitted to the endoscope; and a flexible elastic portion provided around the endoscope insertion port.

In a more specific embodiment of the anti-leak valve unit for overtube according to the present invention, the fitting device may be located at two or more positions with a spacing from each other around the frame portion.

The anti-leak valve unit for overtube according to the present invention may be attached to the overtube including a tube body to be inserted into the body cavity, the base end portion larger in diameter than the tube body, and a expanding portion formed in an increasing diameter from the tube body toward the base end portion; and the fitting device may include a lock portion projecting inwardly of the frame portion, so as to be removably engaged with an outer surface of the expanding portion.

In a more specific embodiment of the anti-leak valve unit for overtube according to the present invention, the fitting device may further include a finger-engaging portion integrally formed with the lock portion, for switching the lock portion between a closed state that enables engagement with the expanding portion and an open state that enables removal from the expanding portion.

In a more specific embodiment of the anti-leak valve unit for overtube according to the present invention, the endoscope insertion port may include a straight tube portion extending thicknesswise of the valve element.

In a more specific embodiment, the anti-leak valve unit for overtube according to the present invention may comprise a generally ring-shaped fixing member that fixes the valve element to the frame portion.

In a more specific embodiment of the anti-leak valve unit for overtube according to the present invention, the elastic portion may include a bellows portion.

In a more specific embodiment, the anti-leak valve unit for overtube according to the present invention may comprise a reinforcing member provided between an outer periphery of the endoscope insertion port and an inner periphery of the elastic portion.

In a more specific embodiment of the anti-leak valve unit for overtube according to the present invention, the reinforcing member may be of an O-ring shape.

In a more specific embodiment of the anti-leak valve unit for overtube according to the present invention, an inner diameter of the endoscope insertion port may be smaller than an outer diameter of the endoscope, by equal to or more than 0 mm and equal to or less than 5 mm.

In a more specific embodiment, the anti-leak valve unit for overtube according to the present invention may further comprise a second valve element including a second endoscope insertion port and a second elastic portion, located on a distal end side of the valve element, with a spacing therefrom.

In a more specific embodiment of the anti-leak valve unit for overtube according to the present invention, the second endoscope insertion port may be a hole or a slit through which the endoscope can be loosely inserted.

It is to be noted that the constituents of the present invention do not have to be individually independent, but may be configured such that a plurality of constituents constitutes a single member, a constituent is composed of a plurality of members, a constituent is a part of another constituent, a part of a constituent and a part of another constituent overlap, and so forth.

The present invention provides an anti-leak valve unit for overtube that allows extracting a diseased tissue without damaging the same in endoscopic mucosal resection, and preventing leakage of supplied air despite a back and forth or rotational movement of the endoscope, and that can be easily attached and removed to and from the overtube.

BRIEF DESCRIPTION OF THE DRAWINGS

The above and other objects, features and advantages will be more apparent from the following preferred embodiment and the accompanying drawings.

BEST MODE FOR CARRYING OUT THE INVENTION

Figure 1:
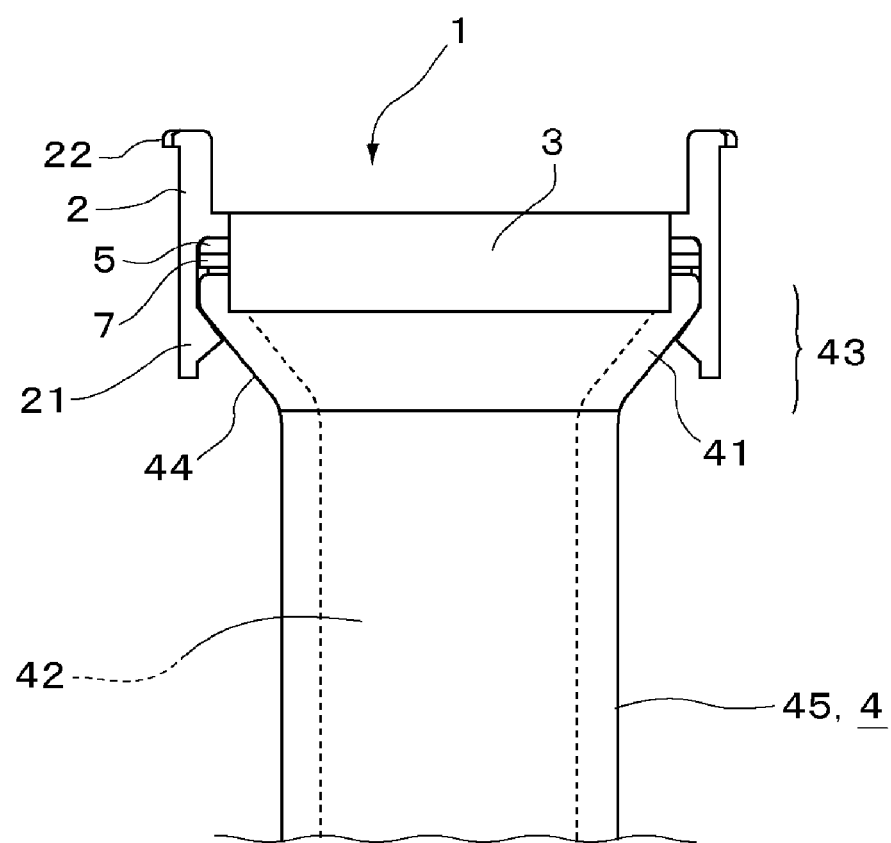
FIG. 1 is a front view of an anti-leak valve unit according to an embodiment of the present invention, attached to an overtube for endoscope.

Hereunder, an embodiment of the anti-leak valve unit for overtube (hereinafter, simply "anti-leak valve unit" as the case may be) according to the present invention will be described referring to the drawings. In all the drawings, common constituents are given the same numeral, and detailed description thereof will not be repeated in the subsequent description.

The anti-leak valve unit 1 according to this embodiment is removably attached to a base end portion 43 of an overtube 4 that includes an inner cavity 42 through which an endoscope (not shown) is to be removably inserted, and that is to be inserted into a body cavity.

The anti-leak valve unit 1 includes a frame portion 3 attached to an outer circumferential surface 44 of the base end portion 43 of the overtube 4, a fitting device 2 provided on the frame portion 3 so as to be removably engaged with the outer circumferential surface 44 of the base end portion 43, and a valve element 5 provided inside the frame portion 3.

The valve element 5 according to this embodiment includes an annular endoscope insertion port 6 located at a generally central portion of the valve element 5 so as to be circumferentially fitted to the endoscope, and a flexible elastic portion 8 provided around the endoscope insertion port 6.

Hereunder, the anti-leak valve unit 1 according to this embodiment will be described in further details.

As shown in FIG. 1, the anti-leak valve unit 1 according to this embodiment is attached to the overtube 4 which includes a tube body 45 to be inserted into the body cavity, the base end portion 43 larger in diameter than the tube body 45, and a expanding portion 41 formed in an increasing diameter from the tube body 45 toward the base end portion 43.

The fitting device 2 of the anti-leak valve unit 1 includes a lock portion 21 projecting inwardly of the frame portion 3, so as to be removably engaged with the outer circumferential surface 44 of the expanding portion 41.

The tube body 45 of the overtube 4 is a finer-diameter portion with an open distal end, to be inserted into a cavity of a human body or the like.

The base end portion 43 is a larger-diameter portion having a predetermined length to be retained outside the body cavity, and the inner cavity 42 is open toward the proximal end of the overtube 4.

In other words, the diameter of the overtube 4 gradually increases from the tube body 45 toward the base end portion 43.

The base end portion 43 may be formed in various shapes, among which typically a circular funnel-like shape is adopted, from the viewpoint of ease of insertion through the endoscope insertion port 6.

Thus, as shown in FIG. 1, the base end portion 43 of the overtube 4 to which the anti-leak valve unit 1 according to this embodiment is attached includes the expanding portion 41 of a tapered shape, where the diameter of the tube body 45 is smoothly increasing.

Here, in this embodiment the base end portion 43 is a region having a predetermined length on the side of the proximal end of the overtube 4, and includes the expanding portion 41 of the tapered shape.

However, the overtube 4 to which the anti-leak valve unit 1 is attached is not limited to the foregoing. For example, the tube body 45 and the base end portion 43 may have the same diameter, and the overtube 4 may include a stepped portion where the diameter discontinuously increases from the tube body 45 toward the base end portion 43.

Figure 2:
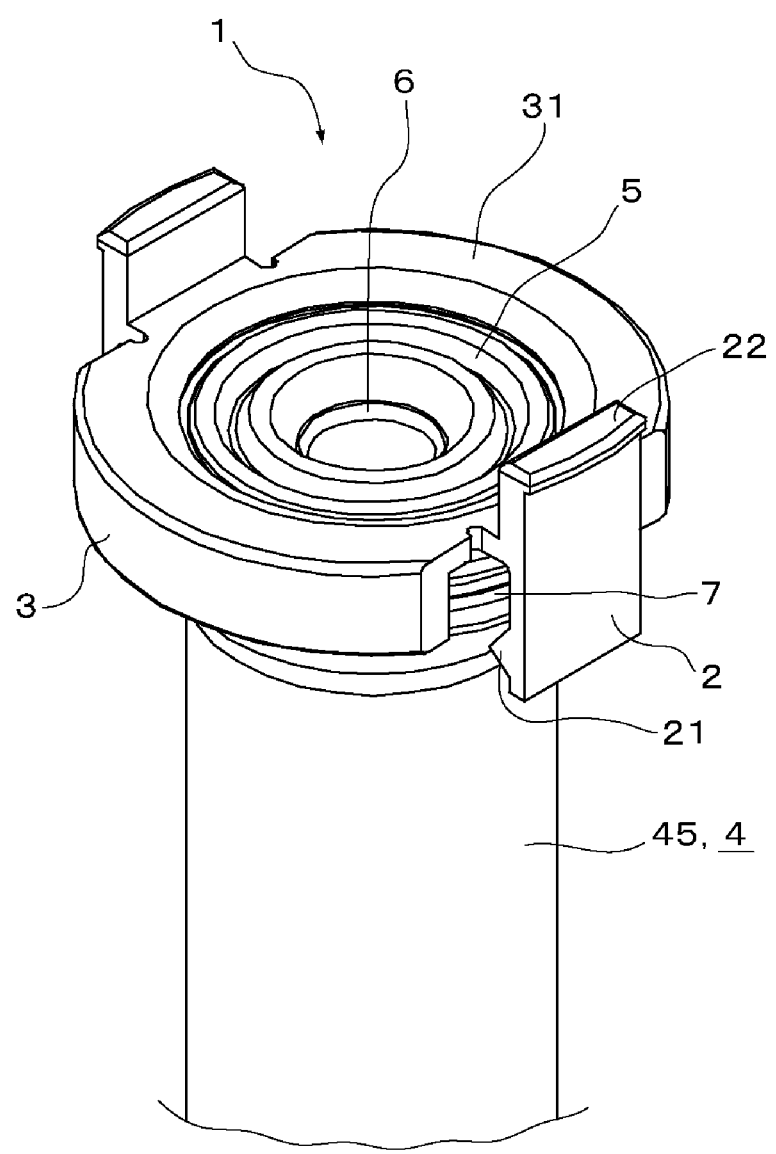
FIG. 2 is a perspective view of the anti-leak valve unit according to the embodiment of the present invention, attached to the overtube for endoscope.
Figure 3:
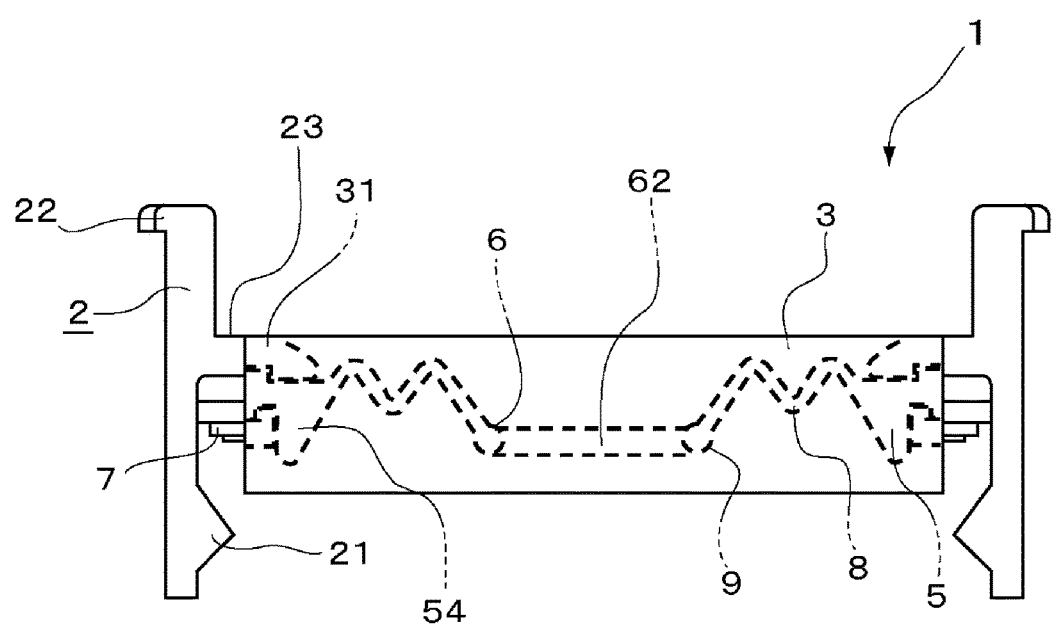
FIG. 3 is a front view of the anti-leak valve unit according to the embodiment of the present invention.

As shown in FIGS. 1 to 3, the frame portion 3 of the anti-leak valve unit 1 is a frame body attached to the outer circumferential surface 44 of the base end portion 43.

The frame portion 3 may be formed in various shapes according to the shape of the base end portion 43 of the overtube 4, among which a generally cylindrical shape is adopted in this embodiment. Also, the frame portion 3 includes a fixing portion 31 integrally formed therewith, in an inwardly projecting flange shape of a predetermined width.

The valve element 5 is a flexible member to be brought into air-tight close contact with the endoscope, located on the inner surface of the frame portion 3. More specifically, the valve element 5 is a generally disk-shaped member independently formed from the frame portion 3, and attached inside the cylindrical frame portion 3 so as to be fixed by the fixing portion 31.

The valve element 5 includes, at a generally central portion thereof, the annular endoscope insertion port 6 having a generally circular insertion hole 62. The endoscope insertion port 6 is elastically stretchable and deformable, so that the endoscope can be removably inserted through the insertion hole 62, and the endoscope insertion port 6 is air-tightly fitted around the endoscope.

Along the outer periphery of the endoscope insertion port 6, an elastic portion 8 is provided. The elastic portion 8 is a soft material that allows the endoscope insertion port 6 to move radially (left and right in FIG. 3), back and forth (up and down in FIG. 3), and rotationally (twisting or pivoting direction of the endoscope). In the anti-leak valve unit 1 according to this embodiment, the elastic portion 8 allows the valve element 5 to be deformed following up the movement of the endoscope. Accordingly, the manipulability of the endoscope is not degraded when the operator moves the endoscope inserted through the inner cavity 42 of the overtube 4.

Figure 6:
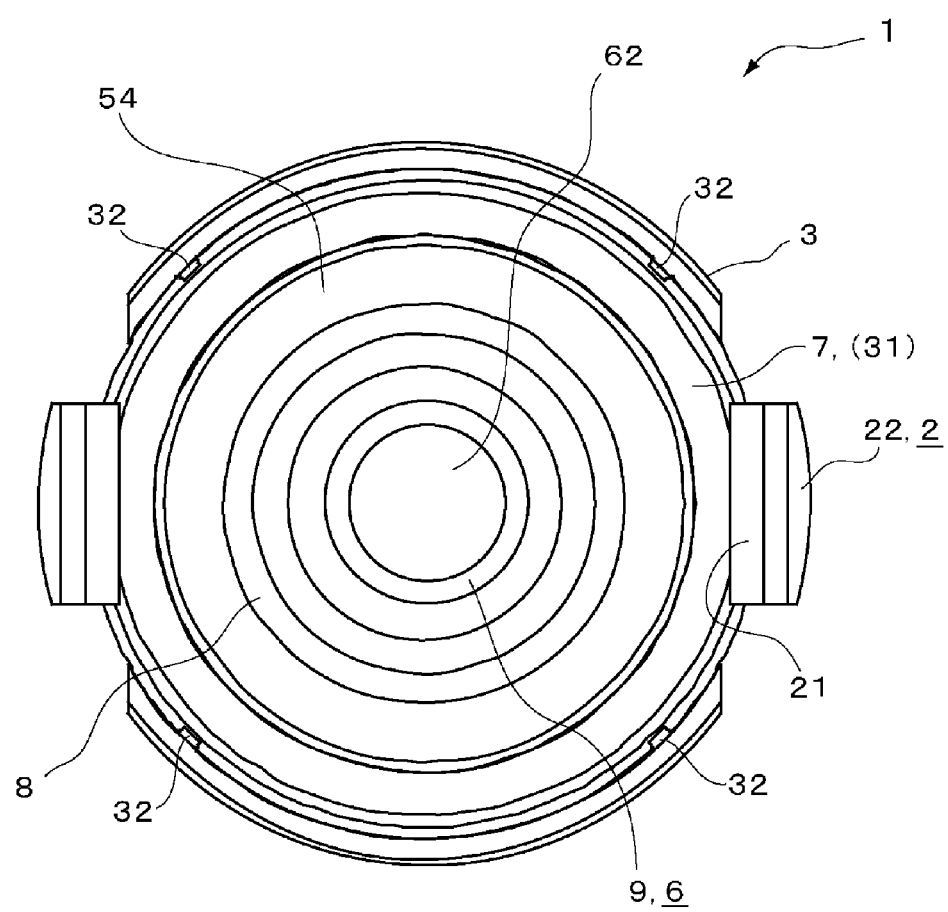
FIG. 6 is a rear view of the anti-leak valve unit according to the embodiment of the present invention.

Along the outer periphery of the valve element 5, a seal portion 54 (ref. FIGS. 3 and 6) integrally formed with the elastic portion 8 is provided, so as to fit with the proximal end opening of the inner cavity 42 of the overtube 4, to thereby air-tightly seal the opening.

The anti-leak valve unit 1 according to this embodiment can be removably attached to the base end portion 43 of the overtube 4 by means of the fitting device 2.

The fitting device 2 is located on the circumference of the outer peripheral edge of the frame portion 3.

The anti-leak valve unit 1 according to this embodiment can be attached to the overtube 4 by engaging the lock portion (lock nail) 21 projecting inwardly of the frame portion 3, with the expanding portion 41 which expands in a tapered shape from the distal end side toward the proximal end side of the overtube 4.

The lock portion 21 according to this embodiment is formed at a tip portion of the fitting device 2 axially projecting from the cylindrical frame portion 3.

However, the present invention is not limited to the foregoing configuration, but the lock portion 21 may be formed, for example, on an inner circumferential surface of the cylindrical frame portion 3.

Also, the lock portion 21 according to the present invention is not limited to the lock nail to be engaged with the expanding portion 41 of the overtube 4. For example, the lock portion 21 may be constituted of a combination of a frictional element such as a silicone rubber having a predetermined friction coefficient and a biasing element such as a spring that biases the frictional element toward the outer circumferential surface 44 of the overtube 4.

The lock portion 21 thus configured allows fixing the anti-leak valve unit 1 to the outer circumferential surface 44 of the base end portion 43, even in the case where the overtube 4 is not provided with the expanding portion 41 with which the lock nail can be engaged.

The anti-leak valve unit 1 according to this embodiment can be removably attached to the outer circumferential surface 44 of the overtube 4 by means of the fitting device 2 which can be removably engaged with the base end portion 43 of the overtube 4. In other words, the anti-leak valve unit 1 according to this embodiment is attached to the outer part of the overtube 4. Such structure prevents reduction of the motion range of the endoscope inside the inner cavity 42 of the overtube 4 when the anti-leak valve unit 1 is attached to the overtube 4, thereby securing full manipulability of the endoscope.

Also, when the anti-leak valve unit 1 is attached to the overtube 4, the valve element 5 fitted around the endoscope keeps the proximal end of the inner cavity 42 air-tightly sealed. Accordingly, pressurized air supplied into the body cavity is inhibited from leaking through the proximal end of the overtube 4, even when the endoscope inserted through the inner cavity 42 is moved back and forth or left and right. Consequently, clear visibility of the diseased part and high operation efficiency of the resection can be secured.

Further, the anti-leak valve unit 1 can be removed from the overtube 4. Accordingly, when the diseased tissue endoscopically resected by EMR or ESD is to be extracted from the body cavity, the anti-leak valve unit 1 can be removed from the overtube 4 with the endoscope remaining inserted through the inner cavity 42. Thus, when taking out the diseased tissue from the inner cavity 42 to the proximal end side, there is no need to pass the diseased tissue through the endoscope insertion port 6 of the valve element 5. Here, since it is not necessary to supply air to the diseased part in general, when extracting the diseased tissue, removing the anti-leak valve unit 1 from the overtube 4 thereby opening the proximal end of the inner cavity 42 causes no problem.

In contrast, the anti-leak valve according to the patent document 2 is pressed into inside of the inner cavity of the overtube, and hence requires forming a special annular groove on the base end portion of the overtube, which degrades versatility. Besides, in the case where such anti-leak valve is attached to a general-use overtube without the annular groove, the motion range of the endoscope is reduced to an extent corresponding to the thickness of the tip portion of the anti-leak valve attached to the overtube.

Further, once the anti-leak valve according to the patent document 2 which is pressed into the inner cavity of the overtube is press-inserted to the inner cavity, the anti-leak valve cannot be easily removed from the overtube. Accordingly, the resected diseased tissue has to be passed through the hole of the valve element, which makes it difficult to extract the resected diseased tissue from the body cavity.

The fitting device 2 includes the finger-engaging portion 22 integrally formed with the lock portion 21. The finger-engaging portion 22 serves for switching the lock portion 21 between a closed state that enables engagement with the expanding portion 41 and an open state that enables removal therefrom.

As shown in FIG. 3, the fitting device 2 includes the lock portion 21 at a lower portion thereof and the finger-engaging portion 22 at an upper portion thereof, and is joined to the frame portion 3 at a joint portion 23 located between the lock portion 21 and the finger-engaging portion 22. The joint portion 23 is movably joined to the frame portion 3, and when an external force is not applied to the finger-engaging portion 22 (closed state) the lock portions 21 opposing each other are fitted to the outer surface of the expanding portion 41 of the overtube 4, so that the anti-leak valve unit 1 is fixed to the overtube 4. By pressing the finger-engaging portion 22 with a finger so as to inwardly tilt toward the central axis of the frame portion 3, the distance between the lock portions 21 opposing each other is increased until exceeding the outer diameter of the expanding portion 41 of the overtube 4 (open state). Such action permits the lock portions 21 to pass over the expanding portion 41 of the overtube 4, thereby enabling removing the anti-leak valve unit 1 from the overtube 4.

The number of the fitting devices 2 is not specifically limited, but the fitting devices 2 may be provided at one position, or two or more positions.

In the anti-leak valve unit 1 according to this embodiment, the fitting device 2 is located at two positions with a spacing from each other around the frame portion 3, as shown in FIG. 2.

To be more detailed, the fitting device 2 according to this embodiment is located at two positions opposing each other across the central axis of the cylindrical frame portion 3.

Alternatively, three fitting devices 2 may be provided at angular intervals of 120 degrees from each other with respect to the central axis of the frame portion 3, or four fitting devices 2 may be provided at angular intervals of 90 degrees from each other with respect to the central axis. Further, the fitting device 2 may be provided at just one position on the circumference of the frame portion 3. In other words, one piece of fitting device 2 and the frame portion 3 may collaborate to fix the anti-leak valve unit 1 to the base end portion 43 of the overtube 4, such that the anti-leak valve unit 1 can be removed from the overtube 4 by releasing the fitting device 2.

It is preferable, in the case where the operator is using either hand to manipulate the endoscope or the endoscopic treatment device, that the anti-leak valve unit 1 according to this embodiment allows the operator to use the other hand to remove the anti-leak valve unit 1 from the overtube 4, and from the viewpoint of ease of the removing action by one hand, it is preferable that the number of fitting device 2 is not greater than three. Further, it is preferable to provide two fitting devices 2 at opposing positions on the circumference of the frame portion 3, since such arrangement allows the operator to open the fitting devices 2 simply by holding the same between the fingers.

Still further details of the anti-leak valve unit 1 according to this embodiment will be described hereunder.

The fitting device 2 may be formed integrally with the frame portion 3, or separately from the frame portion 3 and movably joined and fixed to the frame portion 3. In the case of integrally forming the fitting device 2 and the frame portion 3, a resin material may be employed, for example a rigid vinyl chloride resin, a polyurethane resin, a polyethylene resin, a polyamide resin, a polypropylene resin, a polyacetal resin, or a fluorinated polyethylene resin. In this case, from the viewpoint of durability of the joint portion 23 serving as a hinge between the fitting device 2 and the frame portion 3, it is preferable to employ the polyethylene resin, the polyamide resin, or the polypropylene resin.

In the case of separately forming the fitting device 2 and the frame portion 3, the material of the fitting device 2 is not specifically limited, however it is employ a relatively rigid material since the fitting device 2 has to have sufficient strength to withstand the external force applied to the finger-engaging portion 22 for tilting the entirety of the fitting device 2. Examples of such material for the fitting device 2 include a rigid vinyl chloride resin, a rigid polyurethane resin, a polyethylene resin, a polyamide resin, a polypropylene resin, a polyacetal resin, and a fluorinated polyethylene resin.

In the case of separately forming the fitting device 2 and the frame portion 3, the material of the frame portion 3 is not specifically limited, however it is preferable that the material has sufficient strength to withstand the external force applied to the fitting device 2 without being deformed, to thereby effectively fix the valve element 5. Also, employing a relatively rigid material for the frame portion 3 allows securing a sufficient inner diameter of the inner cavity 42 thereby improving the manipulability of the endoscope. Examples of the material of the frame portion 3 include a rigid vinyl chloride resin, a rigid polyurethane resin, a polyethylene resin, a polyamide resin, a polypropylene resin, a polyacetal resin, and a fluorinated polyethylene resin.

In the case of separately forming the fitting device 2 and the frame portion 3, the fitting device 2 and the frame portion 3 may be joined at the joint portion 23 by means of a hinge joint using a fixing pin provided so as to penetrate through the both parts. Also, a spring may be attached to the fixing pin that biases the lock portion 21 toward the outer circumferential surface 44 of the overtube 4. Such structure allows keeping the fitting device 2 in the closed state without the need of the external force applied by the operator to the fitting device 2, and thereby stably fixing the anti-leak valve unit 1 to the outer circumferential surface 44 of the overtube 4.

Figure 4:
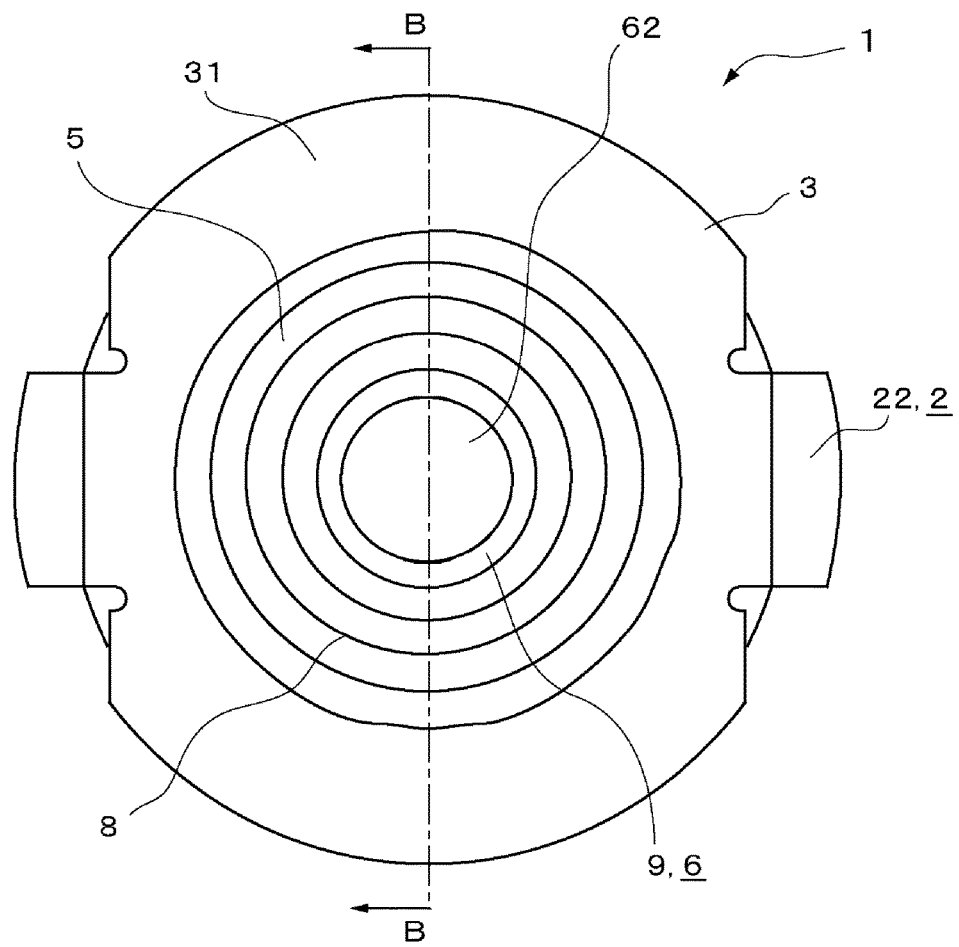
FIG. 4 is a plan view of the anti-leak valve unit according to the embodiment of the present invention.
Figure 5:
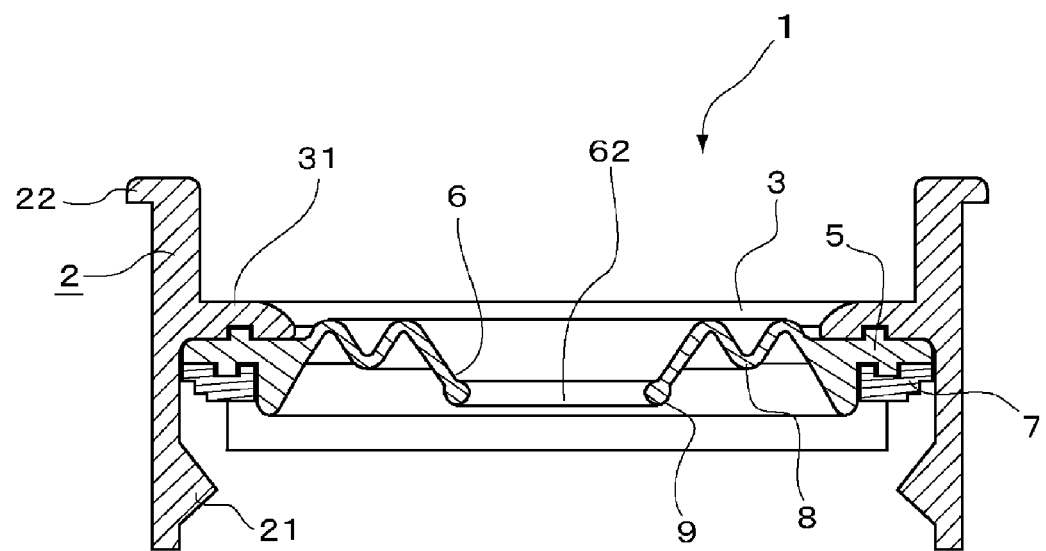
FIG. 5 is a cross-sectional view taken along a line B-B in FIG. 4.

As shown in FIGS. 3 to 5, the anti-leak valve unit 1 according to this embodiment includes the fixing portion 31 that fixes the valve element 5, formed an inwardly projecting flange shape along an end face of one of the openings of the cylindrical frame portion 3. The valve element 5 may be bonded to the fixing portion 31, or retained between the fixing portion 31 and another member.

The anti-leak valve unit 1 according to this embodiment includes a generally ring-shaped fixing member (fixing ring 7) that fixes the valve element 5 to the frame portion 3.

The fixing ring 7 has an outer diameter that enables accommodating the same inside the cylindrical frame portion 3, so that the fixing ring 7 and the fixing portion 31 are pressed against the outer periphery of the valve element 5 so as to hold the same therebetween.

Inside the cylinder constituting the frame portion 3, a nail 32 is provided so as to project therefrom, as shown in FIG. 6. The nail 32 serves as a stopper that prevents the fixing ring 7 from coming off from the frame portion 3.

The material of the fixing ring 7 is not specifically limited, although it is preferable that the material has sufficient strength to firmly fix the valve element 5 to the frame portion 3 and to withstand the friction between the endoscope and the valve element 5, within a limited thickness that suppresses the overall thickness of the anti-leak valve unit 1 so as to improve the manipulability of the endoscope. Specific examples of the material of the fixing ring 7 include a rigid vinyl chloride resin, a rigid polyurethane resin, a polyethylene resin, a polyamide resin, a polypropylene resin, a polyacetal resin, and a fluorinated polyethylene resin.

The anti-leak valve unit 1 according to this embodiment includes a reinforcing member 9 between the outer periphery of the endoscope insertion port 6 and the inner periphery of the elastic portion 8.

The reinforcing member 9 serves to provide higher elastic modulus to the endoscope insertion port 6 than that of the elastic portion 8, to thereby enhance the tightness of the contact with the endoscope.

The reinforcing member 9 according to this embodiment is integrally formed with the annular endoscope insertion port 6 from the common material.

The reinforcing member 9 according to this embodiment is formed in an O-ring shape. Such configuration causes the endoscope insertion port 6 to be uniformly fitted around the endoscope, to thereby prevent formation of a gap between the outer surface of the endoscope and the endoscope insertion port 6, when the endoscope is moved back and forth, up and down or rotationally.

The elastic portion 8 includes a bellows portion that increases and reduces the diameter along a plane that includes the circumference of the insertion hole 62 of the endoscope insertion port 6. Providing the bellows portion in the elastic portion 8 allows alleviating stress applied to the endoscope insertion port 6 especially when the endoscope is inserted and removed, thus enabling smooth insertion and removal thereof. Also, the contracting and stretching motion of the bellows portion keeps free movement of the endoscope from being disturbed, when the endoscope inserted through the insertion hole 62 is moved in any direction including back and forth, up and down and rotationally with respect to the endoscope insertion port 6. Further, since the bellows portion has higher flexibility than the endoscope insertion port 6, the endoscope insertion port 6 is displaced with respect to the frame portion 3 maintaining the close contact with the outer surface of the endoscope. Such configuration allows minimizing the gap between the endoscope insertion port 6 and the endoscope, thereby maintaining the air-tightness between the endoscope and the anti-leak valve unit 1.

First Modification

Figure 7:
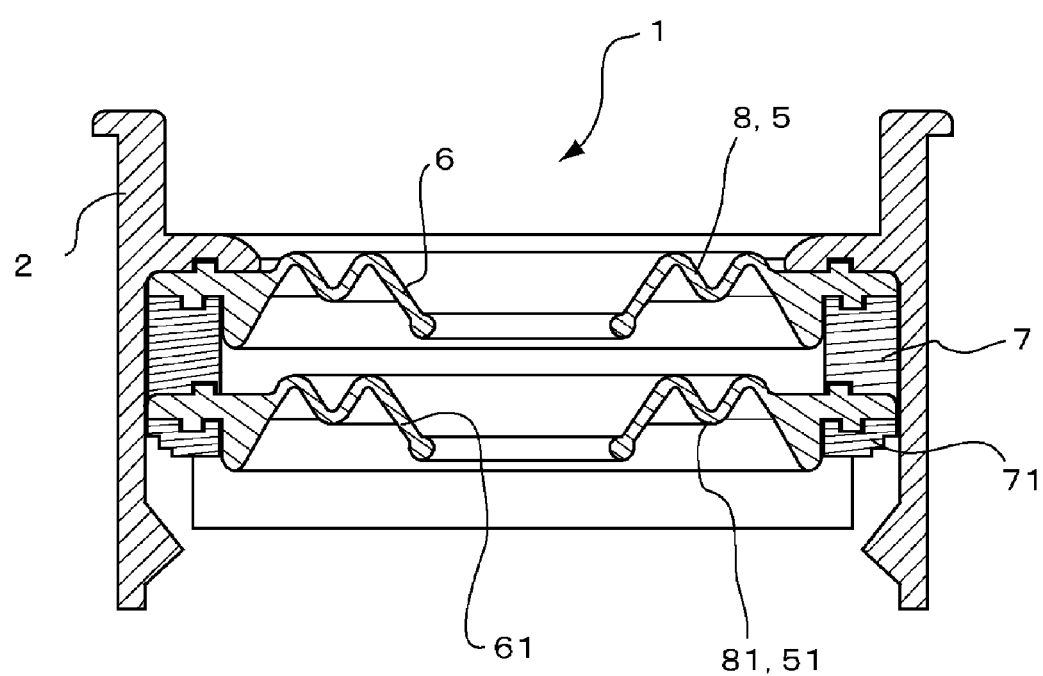
FIG. 7 is a cross-sectional view of an anti-leak valve unit according to a first modification of the present invention.

FIG. 7 is a cross-sectional view of the anti-leak valve unit 1 according to a first modification of this embodiment. As shown therein, the anti-leak valve unit according to this modification includes a second valve element 51 having a second endoscope insertion port 61 and a second elastic portion 81, and located on the distal end side of the valve element (first valve element 5), with a spacing therefrom.

The second valve element 51 is pressed against the first valve element 5 by a second fixing ring 71, so as to be retained therebetween.

Providing thus the second endoscope insertion port 61 allows further assuring the air-tightness between the endoscope and the endoscope insertion port 6. In this case, increasing the thickness of the first fixing ring 7 between the first valve element 5 and the second valve element 51 from the foregoing embodiment (ref. FIG. 5) thereby defining a larger space between the first valve element 5 and the second valve element 51 prevents interference between these valve elements. Such configuration permits free deformation of both the first valve element 5 and the second valve element 51, thereby allowing the both valve elements to more faithfully following up the movement of the endoscope and more effectively maintaining the air-tightness between the endoscope and the endoscope insertion port 6.

The second endoscope insertion port 61 is a hole or a slit through which the endoscope can be loosely inserted. In the case of providing two valve elements as in this modification, it is preferable to make the inner diameter of the endoscope insertion port (6 or 61) of one of the valve elements larger than the outer diameter of the endoscope. Such configuration allows maintaining the manipulability of the endoscope by the operator unchanged, while achieving certain air-tightness with that one of the valve elements.

Second Modification

Figure 8:
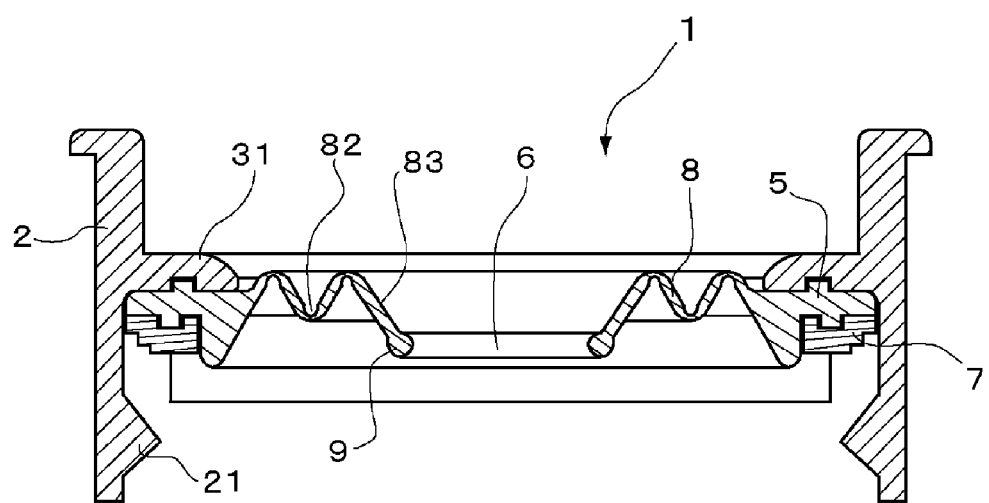
FIG. 8 is a cross-sectional view of an anti-leak valve unit according to a second modification of the present invention.

FIG. 8 is a cross-sectional view of the anti-leak valve unit 1 according to a second modification of the foregoing embodiment. As shown therein, in the elastic portion 8 a hill portion and a valley portion (folded portion 82) of the bellows portion may be made thinner than the remaining straight portion (slope portion 83). Such configuration permits the bellows portion to contract and stretch more flexibly thereby reducing friction with the endoscope when inserting, removing and manipulating the same, which further upgrades the manipulability of the endoscope.

The endoscope is manipulated so as to axially rotate in the endoscope insertion port 6, in addition to movements in the back and forth, up and down, and left and right directions with respect to the endoscope insertion port 6. In this case, against the axial rotational motion in the endoscope insertion port 6, the high elasticity of the thicker slope portion 83 of the bellows portion prevents the endoscope insertion port 6 from rotating together with the endoscope and sticking around the same. Also, the lower elasticity of the thinner folded portion 82 of the bellows portion allows the endoscope insertion port 6 to more effectively follow up the back and forth and left and right movement of the endoscope.

The inner diameter of the endoscope insertion port 6 is smaller than the outer diameter of the endoscope to be inserted therethrough, by equal to or more than 0 mm and equal to or less than 5 mm.

More particularly, it is preferable that the inner diameter of the endoscope insertion port 6 is smaller than the outer diameter of the endoscope, by equal to or more than 2 mm and equal to or less than 4 mm. Making the inner diameter of the endoscope insertion port 6 smaller than the outer diameter of the endoscope in the foregoing range leads to achieving an optimal balance between suppression of resistance against inserting and removing the endoscope and tightness of the contact of endoscope insertion port 6 with the endoscope. Such configuration provides appropriate friction between the endoscope insertion port 6 and endoscope, thereby preventing the anti-leak valve unit 1 from coming off from the overtube 4 together with the endoscope during the manipulation of the same, while preventing leakage of air from the inner cavity 42 caused by the movement of the endoscope.

Preferable examples of the material for the valve element 5 include elastic materials such as natural rubber, synthetic rubber, polyurethane elastomer, styrene-butadiene-styrene terpolymer, and silicone rubber, and it is also preferable that these materials contain oil for optimizing friction with the endoscope.

Third Modification

Figure 9:
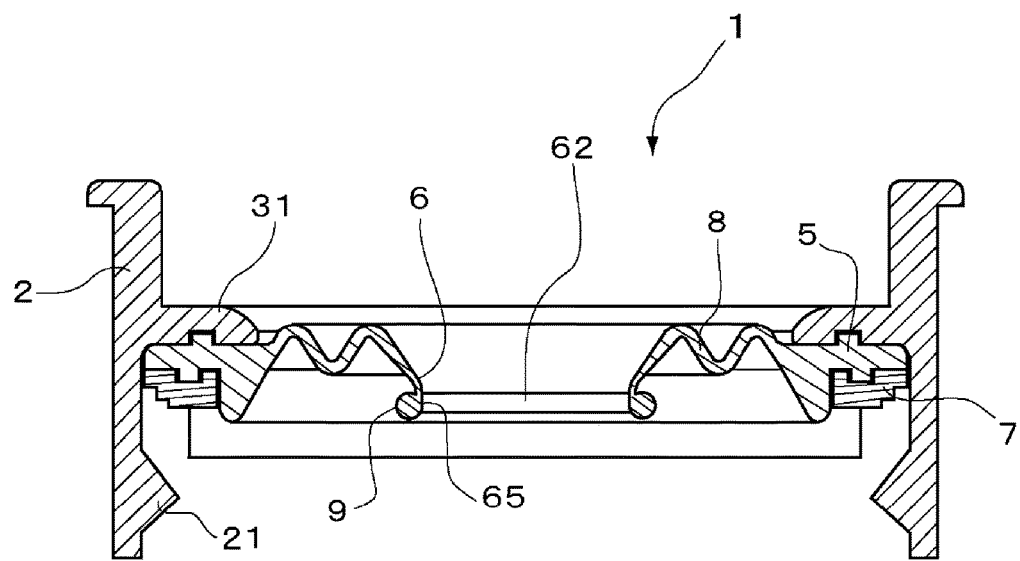
FIG. 9 is a cross-sectional view of an anti-leak valve unit according to a third modification of the present invention.

FIG. 9 is a cross-sectional view of the anti-leak valve unit 1 according to a third modification of the foregoing embodiment.

In the anti-leak valve unit 1 according to this modification, the endoscope insertion port 6 includes a straight tube portion 65 extending thicknesswise of the valve element 5.

The anti-leak valve unit 1 according to this modification is different from that of the foregoing embodiment (ref. FIG. 5) in that the endoscope insertion port 6 is closely fitted to the outer circumferential surface of the endoscope over a predetermined extended length.

The reinforcing member 9 of the O-ring shape is formed along the outer periphery of the straight tube portion 65, and the inner circumferential surface of the straight tube portion 65 is of a cylindrical shape.

The anti-leak valve unit 1 according to this modification enhances the tightness of the contact between the endoscope insertion port 6 and the endoscope, thereby preventing the O-ring shaped reinforcing member 9 from rolling with respect to the endoscope, when the operator moves the endoscope, to which the endoscope insertion port 6 is circumferentially fitted, back and forth with respect to the inner cavity 42. Such configuration prevents appearance of a gap between the endoscope insertion port 6 and the endoscope, when the operator manipulates the endoscope.

The foregoing embodiment encompasses the technical idea according to (i) to (viii) specified hereunder.

(i) An anti-leak valve unit for overtube, to be removably attached to an overtube to be inserted into a body cavity, the overtube including an inner cavity through which an endoscope can be removably inserted, and an expanding portion formed at a base end portion thereof, comprising:

a frame portion of a generally cylindrical shape to be removably attached to an outer circumferential surface of the expanding portion of the overtube;

a fitting device provided at least at two positions on a circumference of an outer periphery of the frame portion, so as to be removably engaged with the outer circumferential surface of the expanding portion; and a generally disk-shaped valve element provided inside the frame portion;

wherein the valve element includes an endoscope insertion port located at a generally central portion of the valve element so as to allow the endoscope to move back and forth and rotationally, while maintaining an air-tight state; and an elastic portion provided around an outer periphery of the endoscope insertion port.

(ii) The anti-leak valve unit for overtube according to (i) above, comprising a generally ring-shaped fixing member that fixes the valve element to the frame portion.

(iii) The anti-leak valve unit for overtube according to (i) or (ii) above, wherein the elastic portion includes a bellows portion.

(iv) The anti-leak valve unit for overtube according to any of (i) to (iii) above, comprising a reinforcing member located between an outer periphery of the endoscope insertion port and an inner periphery of the elastic portion.

(v) The anti-leak valve unit for overtube according to (iv) above, wherein the reinforcing member includes an O-ring.

(vi) The anti-leak valve unit for overtube according to any of (i) to (iii) above, wherein an inner diameter of the endoscope insertion port is smaller than an outer diameter of the endoscope to be inserted, by equal to or more than 0 mm and equal to or less than 5 mm.

(vii) The anti-leak valve unit for overtube according to (i) above, further comprising a second valve element including a second endoscope insertion port and a second elastic portion, located with a spacing from the valve element.

(viii) The anti-leak valve unit for overtube according to (vii) above, wherein the second endoscope insertion port includes either a generally circular hole or a slit formed at a generally central portion of the cap member.

The invention claimed is:

1. A tube assembly, comprising:
an overtube comprising a base end portion formed such that the base end portion has an outer circumferential surface having a large diameter portion and a small diameter portion; and
an anti-leak valve unit comprising a frame body configured to be attached to the base end portion of the overtube and comprising a fixing portion, a plurality of cover portions, and a plurality of fitting portions such that the fixing portion is configured to engage with an end of the base end portion and that the cover portions and the fitting portions are configured to engage with the outer circumferential surface of the base end portion, and a valve element attached to the fixing portion of the frame body such that the valve element is configured to form air-tight contact with an endoscope inserted into the overtube through the fixing portion of the frame body,
wherein the frame body is formed such that the fitting portions are positioned to face each other across the fixing portion and that the cover portions are positioned between the fitting portions, each of the cover portions extends to an end of the large diameter portion of the outer circumferential surface of the base end portion and does not extend beyond the end of the large diameter portion of the outer circumferential surface of the base end portion such that each of the cover portions is configured to engage with the large diameter portion of the outer circumferential surface of the base end portion, and each of the fitting portions extends beyond the end of the large diameter portion of the outer circumferential surface of the base end portion and has a lock nail configured to engage with the small diameter portion of the outer circumferential surface of the base end portion.

2. The tube assembly according to claim 1, wherein the frame body is formed such that the fixing portion, the plurality of cover portions, and the plurality of fitting portions are integrally formed.

3. The tube assembly according to claim 2, wherein the frame body is formed such that the fixing portion, the plurality of cover portions, and the plurality of fitting portions comprise at least one resin selected from the group consisting of a rigid vinyl chloride resin, a polyurethane resin, a polyethylene resin, a polyamide resin, a polypropylene resin, a polyacetal resin, and a fluorinated polyethylene resin.

4. The tube assembly according to claim 3, wherein the valve element comprises at least one material selected from the group consisting of natural rubber, synthetic rubber, polyurethane elastomer, styrene-butadiene-styrene terpolymer, and silicone rubber.

5. The tube assembly according to claim 4, further comprising:
a fixing member configured to fix the valve element to the fixing portion of the frame body,
wherein the valve element has a first convex portion formed on an upper surface of the valve element, and a second convex portion formed on a lower surface of the valve element, the fixing portion of the frame body has a first concave portion into which the first convex portion of the valve element is inserted, and the fixing member has a second concave portion into which the second convex portion of the valve element is inserted.

6. The tube assembly according to claim 3, further comprising:
a fixing member configured to fix the valve element to the fixing portion of the frame body,
wherein the valve element has a first convex portion formed on an upper surface of the valve element, and a second convex portion formed on a lower surface of the valve element, the fixing portion of the frame body has a first concave portion into which the first convex portion of the valve element is inserted, and the fixing member has a second concave portion into which the second convex portion of the valve element is inserted.

7. The tube assembly according to claim 2, wherein the valve element comprises at least one material selected from the group consisting of natural rubber, synthetic rubber, polyurethane elastomer, styrene-butadiene-styrene terpolymer, and silicone rubber.

8. The tube assembly according to claim 7, further comprising:
a fixing member configured to fix the valve element to the fixing portion of the frame body,
wherein the valve element has a first convex portion formed on an upper surface of the valve element, and a second convex portion formed on a lower surface of the valve element, the fixing portion of the frame body has a first concave portion into which the first convex portion of the valve element is inserted, and the fixing member has a second concave portion into which the second convex portion of the valve element is inserted.

9. The tube assembly according to claim 2, further comprising:
a fixing member configured to fix the valve element to the fixing portion of the frame body,
wherein the valve element has a first convex portion formed on an upper surface of the valve element, and a second convex portion formed on a lower surface of the valve element, the fixing portion of the frame body has a first concave portion into which the first convex portion of the valve element is inserted, and the fixing member has a second concave portion into which the second convex portion of the valve element is inserted.

10. The tube assembly according to claim 1, wherein the frame body is formed such that the fixing portion, the plurality of cover portions, and the plurality of fitting portions comprise at least one resin selected from the group consisting of a rigid vinyl chloride resin, a polyurethane resin, a polyethylene resin, a polyamide resin, a polypropylene resin, a polyacetal resin, and a fluorinated polyethylene resin.

11. The tube assembly according to claim 10, wherein the valve element comprises at least one material selected from the group consisting of natural rubber, synthetic rubber, polyurethane elastomer, styrene-butadiene-styrene terpolymer, and silicone rubber.

12. The tube assembly according to claim 11, further comprising:
a fixing member configured to fix the valve element to the fixing portion of the frame body,
wherein the valve element has a first convex portion formed on an upper surface of the valve element, and a second convex portion formed on a lower surface of the valve element, the fixing portion of the frame body has a first concave portion into which the first convex portion of the valve element is inserted, and the fixing member has a second concave portion into which the second convex portion of the valve element is inserted.

13. The tube assembly according to claim 10, further comprising:
a fixing member configured to fix the valve element to the fixing portion of the frame body,
wherein the valve element has a first convex portion formed on an upper surface of the valve element, and a second convex portion formed on a lower surface of the valve element, the fixing portion of the frame body has a first concave portion into which the first convex portion of the valve element is inserted, and the fixing member has a second concave portion into which the second convex portion of the valve element is inserted.

14. The tube assembly according to claim 1, wherein the valve element comprises at least one material selected from the group consisting of natural rubber, synthetic rubber, polyurethane elastomer, styrene-butadiene-styrene terpolymer, and silicone rubber.

15. The tube assembly according to claim 14, further comprising:
a fixing member configured to fix the valve element to the fixing portion of the frame body,
wherein the valve element has a first convex portion formed on an upper surface of the valve element, and a second convex portion formed on a lower surface of the valve element, the fixing portion of the frame body has a first concave portion into which the first convex portion of the valve element is inserted, and the fixing member has a second concave portion into which the second convex portion of the valve element is inserted.

16. The tube assembly according to claim 1, further comprising:
a fixing member configured to fix the valve element to the fixing portion of the frame body,
wherein the valve element has a first convex portion formed on an upper surface of the valve element, and a second convex portion formed on a lower surface of the valve element, the fixing portion of the frame body has a first concave portion into which the first convex portion of the valve element is inserted, and the fixing member has a second concave portion into which the second convex portion of the valve element is inserted.

17. The tube assembly according to claim 16, further comprising:
a second valve element attached to the fixing portion of the frame body such that the second valve element is configured to form air-tight contact with the endoscope inserted into the overtube through the fixing portion of the frame body; and
a second fixing member configured to fix the second valve element to the fixing portion of the frame body.

18. The tube assembly according to claim 16, wherein the fixing member is a fixing ring configured to fix the valve element to the fixing portion of the frame body.

19. The tube assembly according to claim 1, further comprising:
a second valve element attached to the fixing portion of the frame body such that the second valve element is configured to form air-tight contact with the endoscope inserted into the overtube through the fixing portion of the frame body.

20. The tube assembly according to claim 1, wherein each of the fitting portions has the lock nail at one end and a finger-engaging portion at an opposite end.

* * * * *